United States Patent
Minami

(10) Patent No.: US 10,722,390 B2
(45) Date of Patent: Jul. 28, 2020

(54) STENT MADE OF POLYMER MATERIAL HAVING RATCHET

(71) Applicant: Yamaguchi University, Yamaguchi (JP)

(72) Inventor: Kazuyuki Minami, Yamaguchi (JP)

(73) Assignee: Yamaguchi University, Yamaguchi (JP)

(*) Notice: Subject to any disclaimer, the term of this patent is extended or adjusted under 35 U.S.C. 154(b) by 130 days.

(21) Appl. No.: 15/323,434

(22) PCT Filed: Jul. 1, 2015

(86) PCT No.: PCT/JP2015/069060
§ 371 (c)(1),
(2) Date: Jan. 3, 2017

(87) PCT Pub. No.: WO2016/002857
PCT Pub. Date: Jan. 7, 2016

(65) Prior Publication Data
US 2017/0128245 A1    May 11, 2017

(30) Foreign Application Priority Data
Jul. 4, 2014 (JP) .................................. 2014-138602

(51) Int. Cl.
*A61F 2/93*    (2013.01)
*A61F 2/915*    (2013.01)
(Continued)

(52) U.S. Cl.
CPC ............. *A61F 2/93* (2013.01); *A61F 2/856* (2013.01); *A61F 2/915* (2013.01);
(Continued)

(58) Field of Classification Search
CPC ........................................................ A61F 2/93
See application file for complete search history.

(56) References Cited

U.S. PATENT DOCUMENTS

| 5,797,951 A | 8/1998 | Mueller |
| 5,984,963 A | 11/1999 | Ryan et al. |

(Continued)

FOREIGN PATENT DOCUMENTS

| JP | H07-000531 | 1/1995 |
| JP | 2002540841 | 12/2002 |

(Continued)

OTHER PUBLICATIONS

"International Search Report (Form PCT/ISA/210) of PCT/JP2015/069060", dated Oct. 6, 2015, with English translation thereof, pp. 1-4.

*Primary Examiner* — Leslie Lopez
(74) *Attorney, Agent, or Firm* — JCIPRNET

(57) ABSTRACT

A plurality of branch bars is provided on opposing sides of paired strut pieces connected by links in a strut to protrude from one towards the other side, and a plurality of ratchet teeth is formed on the side of the branch bars respectively. When a stent made of polymer material having a cylindrical constitution in which a plurality of struts is connected by links is deformed to enlarge its diameter, the paired struts are deformed to come near to each other, so that the branch bars overlap each other with the ratchet teeth formed thereon engaging with each other. As the effect of engagement of the ratchet teeth with each other, while deformation of the struts so as to enlarge the diameter of the stent is allowed, deformation so as to reduce the diameter of the stent is inhibited.

4 Claims, 7 Drawing Sheets

(51) Int. Cl.
*A61F 2/856* (2013.01)
*A61F 2/06* (2013.01)

(52) U.S. Cl.
CPC .................. *A61F 2002/067* (2013.01); *A61F 2002/91558* (2013.01); *A61F 2002/91566* (2013.01); *A61F 2002/91583* (2013.01); *A61F 2230/0069* (2013.01)

(56) References Cited

U.S. PATENT DOCUMENTS

| | | | | |
|---|---|---|---|---|
| 6,964,680 | B2 * | 11/2005 | Shanley | A61F 2/91 623/1.15 |
| 2010/0256740 | A1 * | 10/2010 | Limon | A61F 2/91 623/1.16 |

FOREIGN PATENT DOCUMENTS

| | | |
|---|---|---|
| JP | 2006068250 | 3/2006 |
| JP | 2008200530 | 9/2008 |
| JP | 2011251117 | 12/2011 |

* cited by examiner

Fig.5 (a)
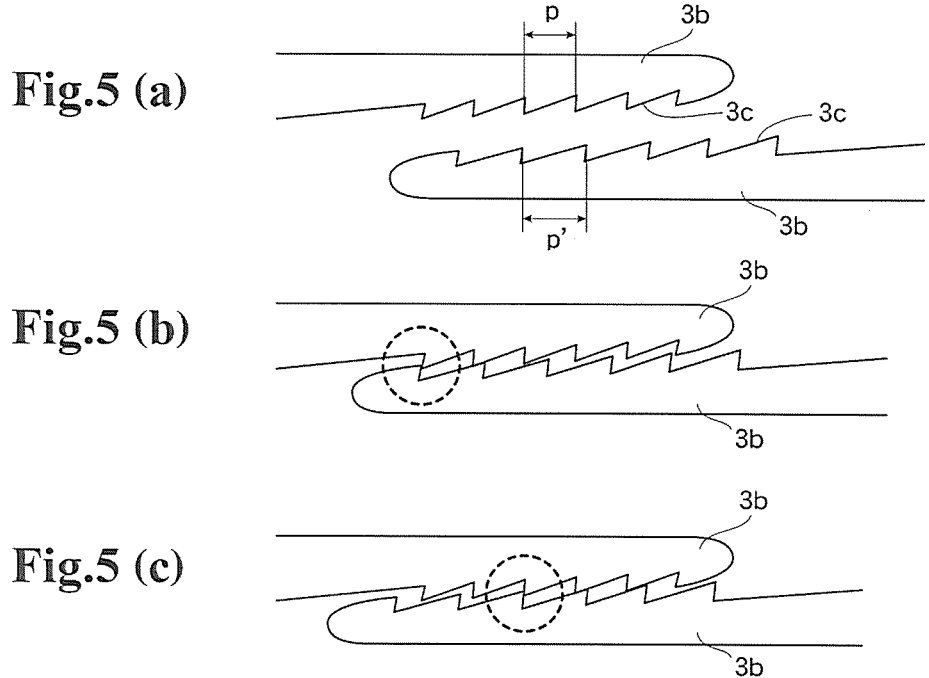
Fig.5 (b)
Fig.5 (c)
Fig.6
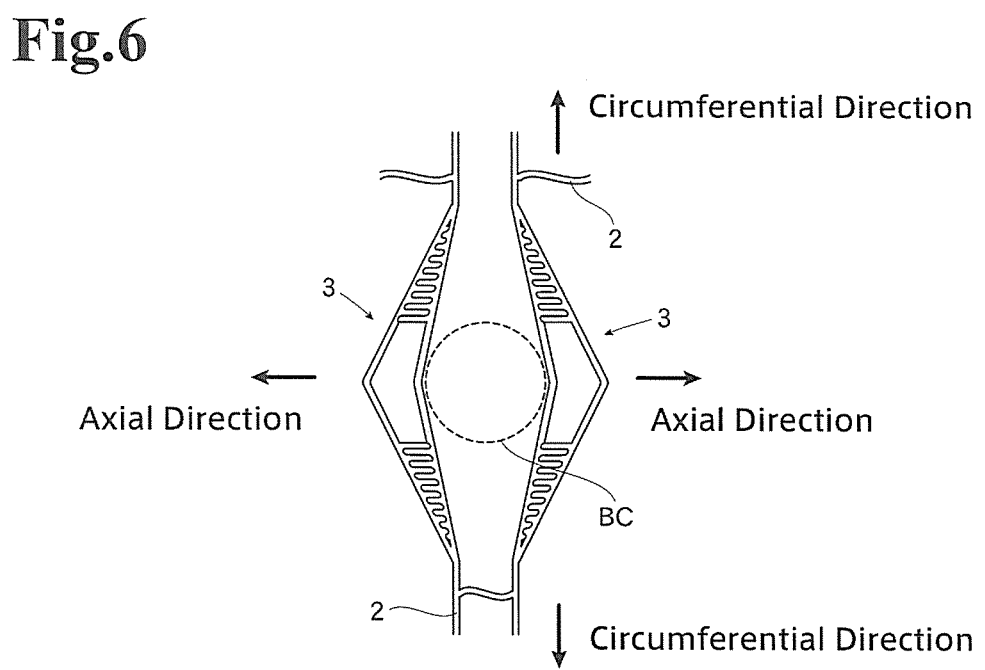

STENT MADE OF POLYMER MATERIAL HAVING RATCHET

CROSS-REFERENCE TO RELATED APPLICATION

This application is a 371 application of International PCT application serial no. PCT/JP2015/069060, filed on Jul. 1, 2015, which claims the priority benefit of Japan application no. 2014-138602, filed on Jul. 4, 2014. The entirety of each of the above mentioned patent applications is hereby incorporated by reference herein and made a part of this specification.

FIELD OF THE INVENTION

The present invention relates to a stent made of polymer material having ratchet.

BACKGROUND OF THE INVENTION

A blood vessel is expanded with a balloon catheter to indwell a stent therein for treatment of diseases relating to the disorder of blood vessels such as myocardial infarction or cerebral infarction. While stents made of metal material are commonly used as such stents, these metal stents are retained in the body permanently. Due to this, a stent made of metal material cannot be applied to a person not in maturity whose physical structure of the body is changed over time, and there is a risk of recurrence of stenosis due to long-term mechanical stimulation.

Stents made of polymer materials do not have such defect as compared with the stents made of metal materials. Stents made of biodegradable polymers have an advantage that solves the problem of stress caused by the stent that is retained in the body permanently, so they are frequently utilized in recent years.

Techniques regarding stents made of polymer material are disclosed in the following documents. Patent Document 1 discloses a ladder-shaped expandable stent formed by connecting a plurality of ladder elements serially, in which each ladder element enables two longer ribs to slide, the distance between the end side cross rails in neighboring ladder elements is made variable so that the stent can be expanded from a reduced diameter to an expanded diameter and slide back to a reduced diameter is inhibited. Patent Document 2 discloses a stent used in lumens formed of a cylindrical sheet that has a series of protrusions and holes locking each other and provides overlapping end sides so as to create ratchet action when the stent is brought to an expanded state for supporting a portion of an inner wall of a lumen.

Patent Document 3 discloses a stent made of polymer material formed by connecting a plurality of T-shaped units, each of which consists of a head portion and an elongated body portion extending from the head portion, such that one side or both sides of each body portion has at least one protrusion and the head portion has an opening for allowing the body portion to pass through and latching its protrusion.

Patent Document 4 discloses a stent made of polymer material formed by connecting a plurality of T-shaped units, each of which consists of a head portion and an elongated body portion extending from the head portion, such that one side of each body portion has ratchet protrusions and the head portion has a slit for allowing the body portion to pass through and latching its ratchet protrusions, wherein movement of the body portion towards reduction of the diameter of the stent is inhibited and movement of the body portion towards expansion of the diameter of the stent is allowed, either by providing a width changeable portion on the other side of the body portion or by making the connecting portion around the slit in the head portion elastically deformable to change the tilt angle of the slit.

The ladder-shaped expandable stent in Patent Document 1 has a complex shape and structure and has a possibility that the diameter of the stent cannot be varied easily because of large resistance applied on the long ribs. Further, tab stops are provided on the longer ribs to prevent the longer ribs from sliding in the direction that the diameter of the stent is to be reduced and the end side cross rails are engaged to the tab stops, whereas the longer ribs and the end side cross rails are arranged to be at a right angle. For this sake, action of the tab stops induced by movement of the longer ribs may cause the end side cross rails to be distorted and cause the stent to be deformed. The stent according to Patent Document 2 is formed to be a cylindrical sheet, so that the rigidity of the stent is high. Further, ends of the cylindrical sheet protrude outwards, so that it is difficult to make its sectional shape to be circular in a lumen and there is a possibility of being unable to stick fast to the inner wall of the lumen.

Patent Document 3 is proposed by the present inventor to solve problems such as in Patent documents 1 or 2. According to this, strong pressure is applied to the stent made of polymer material from its inside when it is expanded by a balloon and the head portion is placed on the body portion at the site where the body portion pass through the slit. For this sake, deformation of the stent occurs with friction at this site and pressure from inside to cause the linear cut line continuing from the slit to be deformed with expansion so that there is a possibility in which ratchet protrusions are not locked by the slit and movement towards the direction of reduction of the diameter of the stent cannot be withstood, that is, function of the stent is impaired.

Patent Document 4 is proposed by the present inventor, making further improvement. According to this, movement of the body portion towards reduction of the diameter of the stent is inhibited and movement of the body portion towards expansion of the diameter of the stent is allowed, by providing a width changeable portion on the side of the body portion where ratchet protrusions are not formed, by making the tilt angle of the slit in the head portion elastically variable or by making the connecting portion around the slit in the head portion elastically deformable. On the other hand, this is similar to Patent Documents 1 to 3 in that the stent is formed by winding up a sheet material of stent into a cylindrical stent. Degree of freedom in the direction normal to the sheet face is high in stents formed by winding up a sheet material of stent into a cylindrical stent, so that there is a possibility of being unable to stably lock the stent when force in this direction is applied in a case where the stent is used for a long time.

Further, as a common case, a stent is to be indwelled in a main vessel and a branch vessel, when the stent is applied to a site of disease at a branched portion of a blood vessel. T-stent operation, as a method for indwelling a stent in a branched portion of a blood vessel, is a simple technique consisting of indwelling a stent in a branch vessel for first and then indwelling another stent in a main vessel, after which both stents are expanded simultaneously. While this operation is adapted to the case where the angle of the branch vessel is no less than 70 degrees, typically near 90 degrees, there is a disadvantage such that an area is created that cannot be covered with the stent at the site entering the branch vessel when the angle of the branch vessel is small.

Culotte stent operation will be explained referring to FIG. 12 (a) to FIG. 12(c).

FIG. 12 (a) shows a state where a stent S1 is indwelled at a branched portion in a main vessel of a blood vessel so as to extend covering the branched portion. Then, as shown in FIG. 12 (b), another stent S2 is introduced to the branch vessel, widening the struts at the position of the side of the stent S1 facing the branch vessel with the balloon catheter mounting the another stent S2. After this, by expanding both stents simultaneously, a state where stents are indwelled in the main vessel and the branch vessel respectively is attained, as shown in FIG. 12 (c). This technique, enabling the portion entering into the branch to be fully covered with the stents, is adapted also to the case where the angle of the branch vessel is small.

When a stent is to be indwelled in a branch vessel of a blood vessel in such a manner as introducing another stent to the branch vessel, pushing aside the struts on the side of the stent, and the stent is one made of metal material, the configuration of the stent is preserved with plastic deformation and the struts are bent to have a configuration enabling further expansion exceeding the diameter of the blood vessel. In contrast to this, if the stent is one made of polymer material, the struts become to be a straight elongated state when the stent is expanded to the diameter of the blood vessel, so that it is not possible to widen the struts on the side of the stent. This situation is similar in case of a stent made of polymer material as disclosed in Patent Documents 1 to 4. Thus, these are not adapted to indwelling a stent at a branched portion of a blood vessel.

PRIOR ART DOCUMENTS

Patent Documents

Patent Document 1: JP Published Patent Application 2002-540841
Patent Document 2: JP Published Patent Application H07-531
Patent Document 3: JP Published Patent Application 2006-68250
Patent Document 4: JP Published Patent Application 2011-251117

Problems to be Solved by the Invention

A stent made of metal material, as a stent used by indwelling in a lumen after operation for treating disease of a circulatory system, is superior in strength but inferior in flexibility. It is apt to give a mechanical stimulus or stress to the wall of a blood vessel, bringing hyperplasia of the wall of a blood vessel. Beside these, it remains in the body permanently, so that images by MRI (Magnetic Resonance Imaging) is affected in a state where a stent made of metal material remains in the body, thus causing diagnosis to be difficult.

A stent made of polymer material, being able to restrain stress as a problem in a stent made of metal material, has possibility of reducing its diameter after indwelling in a case of a stent expanded by a balloon, because it has a low ability of restraining reduction due to its lower elasticity and strength compared with one made of metal material, and rather easily create creep deformation. With a self-expanding stent, eternal deformation can be generated in a case where it is held to be in a reduced state for a long time or reduction rate is made large, so that there is a possibility of being unable to self-expand.

Further, stents are indwelled in a main vessel and a branch vessel of a blood vessel in a case where stents are applied to treatment of disease that occurred in a branched portion of a blood vessel. At this, it is necessary to make another stent for indwelling in a branch vessel pass through the lateral side of a stent in a main vessel. A stent made of metal material having a network constitution can hold the cylindrical shape of the stent, even if a part of the network constitution on the lateral side of the stent is widened, and can be applied to indwelling in the branch vessel. In contrast to this, a stent made of polymer material formed as a cylindrical stent by winding up a sheet in which a plurality of sets of a head portion and a body portion are interconnected has an inferiority in holding the cylindrical shape of the stent because the body portion is expanded to lateral direction, so that the stent cannot be easily applied to indwelling in a branch vessel.

Means for Solving the Problems

The present invention is attained to solve the above mentioned problems. The stent made of polymer material having ratchet according to the first aspect of the present invention is formed to have a cylindrical shape as a whole in which a plurality of struts, each of which comprises a plurality of strut pieces connected to each other, are connected by links to form a network constitution; wherein the plurality of strut pieces in each of the strut include at least one paired strut pieces, a plurality of branch bars is provided on both opposing sides of the paired strut pieces respectively so as to protrude from one of the strut piece towards the other of the strut piece, a plurality of ratchet teeth is formed on one side or both sides of each of the plurality of branch bars, movement towards opening of the paired strut pieces is inhibited so that deformation of the stent to reduce the diameter of the cylindrical shape of the stent is also inhibited by engagement of the ratchet teeth formed on the branch bars on one of the strut pieces and the ratchet teeth formed on the branch bars on the other one of the strut piece of the paired strut pieces with each other, and movement towards closing of the paired strut pieces towards is allowed so that deformation of the stent to enlarge the diameter of the cylindrical shape of the stent is also allowed.

In the second aspect of the present invention, the stent made of polymer material having ratchet has a feature such that, in the first aspect, the paired strut pieces in each of the plurality of struts are connected by a link in a circumferential direction of the stent to form a Y shape.

In the third aspect of the present invention, the stent made of polymer material having ratchet has a feature such that, in the first aspect, the network constitution in which the plurality of struts is connected by links is configured such that:

the stent made of polymer material has a maximum expanded diameter larger than an inner diameter of a site where the stent is to be indwelled, and when a catheter is introduced between the two struts disposed in a neighboring relation in an axial direction of the stent, the two struts disposed in the neighboring relation are deformed to be elongated in a circumferential direction of the stent as well as deformed to enlarge a distance between the two struts in the axial direction of the stent so that a configuration of the struts and the links is maintained to allow the catheter and another stent made of polymer material to be indwelled thereafter to pass through.

In the fourth aspect of the present invention, the stent made of polymer material having ratchet has a feature such that, in the second or third aspect, the network constitution in which the plurality of struts is connected by links is configured such that:

a set of two of the struts disposed in a neighboring relation in an axial direction of the stent is connected to one of two links that in turn are connected to the link that form the Y shape in the circumferential direction, the plurality of branch bars with ratchet teeth formed thereon are further provided to protrude out from outer sides of the strut pieces on sides where the two struts come close, in the first step of deformation to enlarge the diameter of the stent, deformation is made to cause the set of two of the struts to come close to each other and to cause the ratchet teeth on the branch bars on the outer sides of the two struts to engage with each other, and in the next step, the two struts are deformed to be elongated in the circumferential direction of the stent and to reduce the width of the stents in the axial direction of the stent so that the ratchet teeth on opposed inner sides of the two strut pieces of each of the two struts engage with each other.

In the fifth aspect of the preset invention, the stent made of polymer material having ratchet has a feature such that, in any of the second to fourth aspect, the network constitution in which the plurality of struts is connected by links is configured such that:

a complementary strut in which a plurality of strut pieces is connected by links is disposed between each of the two struts disposed in a neighboring relation in an axial direction of the stent, the strut pieces in the complementary struts have no branch bars provided on sides of the complementary struts, and each two strut pieces on an upper side or a lower side in the complementary strut are connected with links in the circumferential direction of the stent to form an umbrella shape, and in deformation to enlarge the diameter of the stent made of polymer material, the struts on both sides of the complementary strut are elongated in the circumferential direction of the strut, the complementary strut is deformed to enlarge a width of the complementary strut in the axial direction of the stent and then to press the struts on the both sides of the complementary strut in the axial direction of the stent, to promote an effect of advancing engagement of the ratchet teeth formed on the branch bars provided on the sides of the paired strut pieces for the struts on the both sides.

In the sixth aspect of the present invention, the stent made of polymer material having ratchet has a feature such that, in the first aspect, the network constitution in which the plurality of struts is connected by links is configured such that:

the paired strut pieces in each of the plurality of struts are connected to links in a circumferential direction of the stent to form an umbrella shape or a substantially T shape, the plurality of branch bars is provided to protrude on the sides of the paired strut pieces opposite to the sides connected to the link and the plurality of ratchet teeth is formed on one side or both sides of each of the branch bars, and in deformation to enlarge the diameter of the stent made of polymer material, the paired strut pieces are pulled up by the connected links in the circumferential direction of the stent so that the umbrella shape or the substantially T shape of the strut pieces with the link is deformed to become a Y shape, after which the ratchet teeth formed on one side or both sides of the branch bars protruding on the sides of the paired strut pieces come to engage with each other.

In the seventh aspect of the present invention, the stent made of polymer material having ratchet has a feature such that, in the first aspect, the network constitution in which the plurality of struts is connected by links is configured such that:

at least one pair of the paired strut pieces are arranged such that one strut piece more easily deflected to be bent and one strut piece less easily deflected to be bent are spaced apart in the circumferential direction of the stent and connected to each other at end sides, in deformation to enlarge the diameter of the cylindrical shape of the stent made of polymer material, the more easily deflected strut piece of the paired strut pieces is deflected by being pulled up in the circumferential direction of the stent via the connected link so as to come close to the less easily deflected strut piece, thus bringing a state where the branch bars protruding from one side of the more easily deflected strut piece and protruding from the other side of the less easily deflected strut piece are brought into contact with each other, wherein the ratchet teeth formed on the sides of the branch bars are engaged with each other.

In the eighth aspect of the present invention, the stent made of polymer material having ratchet has a feature such that, in any of the first to seventh aspects, the plurality of ratchet teeth formed on one side or both sides of the branch bars provided to protrude on the opposing sides of the paired strut pieces are configured such that the pitch of the ratchet teeth formed on one branch bar is different from the pitch of the ratchet teeth formed on the other branch bar that is engaged with each other.

In the ninth aspect of the present invention, the stent made of polymer material having ratchet has a feature such that, in any of the first to eighth aspects:

in each connecting portions of the strut pieces with the links or in each bending portions between two strut pieces related to deformation of opening-closing, elongation or bending in the strut during deformation to enlarge or reduce a diameter of the stent, a width of each strut piece partly becomes smooth and thin.

Advantageous Effect of the Invention

The stent made of polymer material according to the present invention has a network strut-link constitution in which a plurality of struts is connected by links to be distributed and branch bars having ratchet teeth are provided on the opposing sides of two struts connected commonly by a link at one end respectively. With such arrangement, the stent made of polymer material can be deformed so as to expand the diameter of the stent. On the other hand, when the stent is to be deformed so as to reduce the diameter after expansion by a certain amount, the ratchet teeth on the branch bars provided on the sides of two opposing struts are engaged with each other, so that deformation of the stent to reduce the diameter of the stent is blocked.

Because the stent is made of polymer material, it hardly applies stress to organs in the body compared with a stent made of metal material and does not affect images by MRI. The stent can be formed by using micromachining of a tube shaped material for a stent. For this sake, the stent does not create such a situation as appears with a stent formed by winding up a sheet material such that surplus friction is generated by sheet materials rubbing each other when the stent expands or bending ability decreases making it difficult to cause the stent to pass thorough a site of the vessel with a small radius of curvature in a state where the stent has been wound up to a reduced diameter of the stent for introducing the stent into a blood vessel. Further, the stent made of polymer material according to the present invention is adapted to application to indwelling them in a main vessel and a branch vessel of a blood vessel having a branched portion, similarly as stents made of metal material.

BRIEF EXPLANATION OF DRAWINGS

FIG. 5 (*a*) a view explaining the relation of the pitches of a plurality of ratchet teeth formed on the branch bars respectively and FIGS. 5 (*b*) and (*c*) are views explaining the states of the ratchet teeth engaged with each other when the pitches are different from each other.

FIG. 6 is a view showing a situation where another stent is caused to pass through the side of a stent of polymer material forcibly pushing aside the struts.

DETAILED DESCRIPTION OF PREFERRED EMBODIMENT

Figure 1:
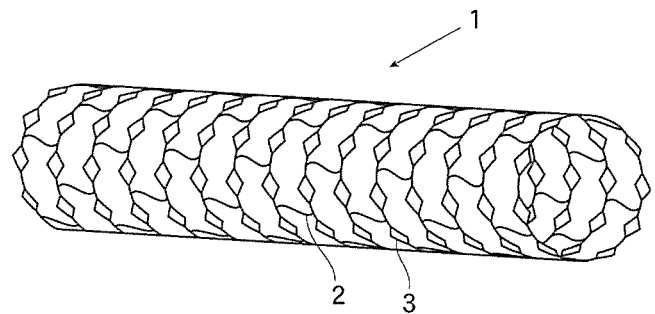
FIG. 1 is a schematic view showing a stent made of polymer material having ratchet according to the present invention.

Embodiments of the stent made of polymer material having ratchet of the present invention will be explained below. FIG. 1 is a schematic view showing a stent with ratchet, in which a stent 1 with ratchet has a network constitution of a cylindrical shape as a whole such that a plurality of struts 3 having a substantially rhombic shape are connected with links 2 respectively.

Figure 2:
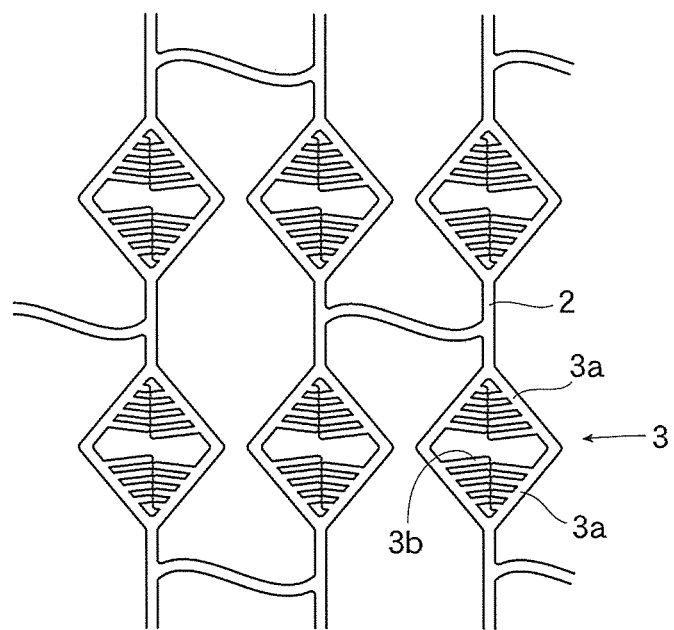
FIG. 2 is an enlarged view showing a part of the stent made of polymer material with ratchet having a network constitution according to FIG. 1.

FIG. 2 is an enlarged view showing a part of the network constitution of the stent 1 having ratchet. Strut pieces 3*a* of each strut 3 form a closed, substantially rhombic shape. A plurality of branch bars 3*b* are provided to protrude on the opposing inner sides of a pair of the strut pieces 3*a* on the upper side as shown respectively and the plurality of branch bars 3*b* are similarly provided to protrude on the opposing inner sides of the paired strut pieces 3*a* on the lower side as shown respectively.

Figure 3:
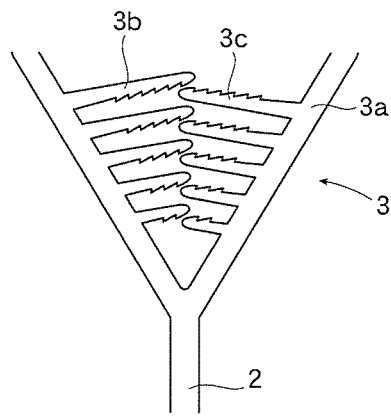
FIG. 3 (*a*) is a further enlarged view showing a substantially Y shaped portion consisting of two struts and a link connecting these shown in FIG. 2, and FIG. 3 (*b*) is a view showing the state of the portion that has been deformed to close the two struts from the state shown in FIG. 3 (*a*).
Figure 3:
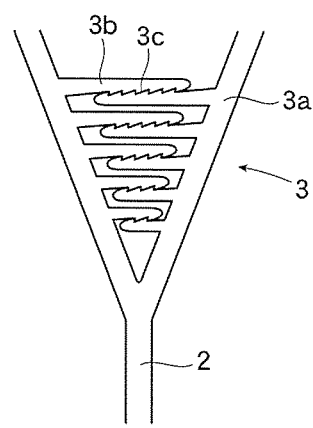

FIG. 3 (*a*) is a further enlarged view showing a substantially Y shaped portion consisting of two strut pieces 3*a* and a link connecting these shown in FIG. 2. A plurality of branch bars 3*b* are provided to protrude inwards on the opposing inner sides of a pair of the strut pieces 3*a* and the branch bars 3*b* protruding out of the pair of left and right struts pieces 3*a* (as shown) are disposed such that corresponding two branch bars 3*b*, one by one out of each strut piece, are mated with each other. As shown in FIG. 3 (*a*), each branch bar 3*b* protruding out of the right strut piece 3*a* is disposed at a slightly downwardly deviated position from corresponding one out of the left strut piece 3*a*. Ratchet teeth 3*c* are formed on one side or both sides of each branch bar 3*b*.

When the stent is deformed in a way that the left and right strut pieces are closed, as shown in FIG. 3 (*b*), the ratchet teeth 3*c* of the mated branch bars 3*b*, which were slightly deviated upwards and downwards each other, come to be engaged with each other. When the stent is deformed in a way that the left and right strut pieces are closed in such a manner, the mated branch bars 3*b* move in a way that the ratchet teeth 3*c* protruding inwards on the sides of one of the mated branch bars 3*b* contact with the ratchet teeth 3*c* of the other of the mated branch bars 3*b* and then both branch bars 3*b* overlap each other. That is, the ratchet teeth 3*c* provided on the mated branch bars 3*b*, each of which protrudes out of either struts piece 3*a*, left or right, come to engage with each other.

In such a manner, the ratchet teeth 3*c* provided on the mated branch bars 3*b*, each of which protrudes out of either struts piece 3*a*, left or right, come to engage with each other. As a result of this, the two strut pieces 3*a* can move in the direction such that the two strut pieces 3*a* are closed from the state of FIG. 3 (*a*) to the state of FIG. 3(*b*). However, the two strut pieces 3*a* cannot move in the reverse direction such that the two strut pieces are opened from the state of FIG. 3 (*b*) to the state of FIG. 3 (*a*) after ratchet teeth 3*c* of the mated branch bars have been engaged with each other. In order to secure the effect of allowing movement in one direction and inhibiting movement in the other direction by causing the ratchet teeth 3*c* on one branch bar 3*b* to engage with the ratchet teeth 3*c* on the other branch bar 3*b*, it is preferable to make a situation such that the sides of the mated branch bars 3*b* where ratchet teeth 3*c* are provided make contact with and push each other to some extent when movement occurs such that strut pieces are closed from the state of FIG. 3 (a) to the state of FIG. 3 (b). Thus, it is important to form the branch bars 3b protruding on the strut pieces 3a so as to have configuration and position satisfying such condition.

While a constitution of the lower part of a substantially rhombic strut 3 shown in FIG. 2 has been explained referring FIG. 3 (a), (b), the upper part of the strut 3 is constituted similarly. That is, in the upper part of the strut 3, branch bars 3b with ratchet teeth 3c provided thereon are similarly provided to protrude inwards on the inner sides of two strut pieces 3a of the substantially Y shaped part, as a part of strut-link network configuration, that is in reversed relation from one shown in FIG. 3 (a). With such arrangement in the upper part of the strut, while the two strut pieces 3a can move in the direction such that the two strut pieces 3a are closed, the two strut pieces 3a cannot move in the reverse direction such that the two strut pieces are opened. The branch bars 3b protruding on the strut pieces 3a in such a manner are provided on each of the all of the struts 3 constituting a network strut-link configuration formed over the whole periphery of the cylindrical stent 1.

While the strut pieces 3a are closed when the diameter of the cylindrical stent 1 made of polymer material changes to become large, the strut pieces 3a is opened when the diameter of the stent 1 made of polymer material changes to become small. The ratchet teeth 3c formed on the branch bars 3b provided to protrude inwards on each strut of the stent 1 made of polymer material engage and mesh with each other when the diameter of the stent has become large to a determined extent to close the strut pieces 3a, so that change of the stent to reduce its diameter is inhibited, while change to enlarge its diameter is allowed.

When the diameter of the stent made of polymer material becomes large in such a manner, the two strut pieces 3a of the substantially Y shaped strut piece-link configuration shown in FIG. 3 (a) are deformed to be closed and the two strut pieces 3a of the substantially Y shaped strut piece in a reversed configuration from one shown in FIG. 3 (a) are deformed similarly to be closed. That is to say, regarding the configuration of the stent made of polymer material as shown in FIG. 2 such that the substantially rhombic struts 3 are connected with links 2, each substantially rhombic strut 3 is deformed as seen in the figure to be elongated longitudinally and be reduced laterally when the stent made of polymer material is deformed so as to enlarge its diameter, while each substantially rhombic strut 3 is deformed adversely as seen in the figure to be reduced longitudinally and be elongated (expand) laterally when the stent made of polymer material is deformed so as to reduce its diameter.

For this sake, remarking the strut pieces 3a of each substantially rhombic strut 3, deformation of opening and closing is caused at the portion of the two strut pieces 3a, 3a connected to one of upper or lower link 2 as shown in FIG. 2. On the other hand, regarding the two left and right strut pieces 3a, 3a connected to be bent in a nearly "<" shape (or a reversed "<" shape) as shown in FIG. 2, deformation is caused in the bending portion in a direction of elongation towards a straight line or reversely in a direction of further bending.

In the connecting portion of two strut pieces with a link or bending portion between two strut pieces where such deformation is caused, stress concentration is apt to be generated and further there is a possibility of bringing rupture. In order to prevent this from occurring, it is effective to form the width of strut pieces in such a portion to become smooth and thin and to be bent in a somewhat curved shape. In such a manner, forming such portions involved in deformation of struts to be thinned smoothly or to have a curved shape makes a contribution to relaxation of stress concentration in such portions or allowing the strut shape to be easily deformed.

Figure 4:
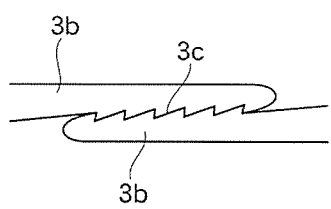
FIG. 4 (*a*) is an enlarged view showing, regarding a set of branch bars, a state of ratchet teeth engaged with each other that protrude on the two mated branch bars respectively when the two struts become closed, and FIG. 4 (*b*) is a view showing another arrangement of ratchet teeth formed to protrude on the struts.
Figure 4:
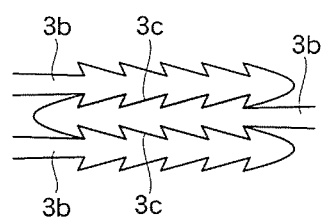

FIG. 4 (a) is a view showing, regarding a set of mated branch bars 3c, a state of ratchet teeth engaging with each other that protrude on the mated two left and right branch bars as shown respectively when the diameter of the stent 1 is enlarged to close two strut pieces 3a from the state in FIG. 3 (a) to the state in FIG. 3 (b).

FIG. 4 (b) is a view showing another arrangement of ratchet teeth 3c on the branch bars 3b formed to protrude on the strut pieces 3a, in which ratchet teeth 3c are provided on both sides of a branch bar 3b as shown. The distance between two neighboring branch bars 3b, 3b provided on one strut piece 3a is preferably equivalent to or slightly narrower than the maximum width (the distance between the tops of the ratchet teeth on the both sides of the branch bar) of a branch bar 3b provided on the other strut piece 3a entering between the two branch bars 3b, 3b on the one strut piece 3a. As seen in FIG. 4 (b), a branch bar 3b on the right strut piece 3a forcibly enters between the neighboring branch bars 3b, 3b of the left strut piece 3a, so that the ratchet teeth 3c on the both sides of the branch bar 3b of the right strut piece 3a engage with the ratchet teeth 3c, 3c on the respective branch bars 3b of the left strut piece 3a positioned on both sides. When the branch bar 3b of the right strut piece 3a forcibly enters between the branch bars 3b, 3b of the left strut piece 3a, the former advances slightly pushing the latter aside and then, at the moment that ratchet teeth 3c are engaged with each other, the branch bars are recovered by elastic force to be in a state shown in FIG. 4 (b). This is similar as seen from the branch bar 3b of the left strut piece 3a. In such a manner, the ratchet teeth 3c on both sides of a branch bar 3b of one strut piece 3a engage with the ratchet teeth 3c on the side of the branch bars 3b of the other strut piece 3a respectively, so that locking force by ratchet teeth comes to be secured further.

As explained above, in an elementary part of a cylindrical stent made of polymer material having a network constitution in which a plurality of struts are connected by links, a substantially Y shaped element is formed with two strut pieces and a link, a plurality of branch bars are provided to protrude on the inner sides of the two strut pieces having an angle between them and connected to the link so that the branch bars of one strut piece protrude towards the branch bars of the other strut piece, and a plurality of ratchet teeth are provided on one side or both sides of these branch bars respectively. The ratchet teeth on the branch bars have a configuration so as to allow the two strut pieces to move to close them with the branch bars from overlapping each other and inhibit the two strut pieces to move to open them by the ratchet teeth engaged with each other. With the action of the ratchet teeth provided on the branch bars, while deformation of a stent made of polymer material such that the diameter of the stent is reduced is inhibited, deformation such that the diameter of the stent is enlarged is allowed.

Regarding the state where the branch bars provided on the strut pieces overlap each other and the ratchet teeth engage with each other as shown in FIG. 4 (a), (b), a plurality of ratchet teeth formed on each branch bar basically have an equal pitch between them, and the figure shows a state such that a plurality of ratchet teeth engage with each other as a whole. While a plurality of ratchet teeth of the overlapping branch bars come to engage with each other as a whole by forming the ratchet teeth of the overlapping branch bars to have an equal pitch. On the other hand, such a case can be also considered that no ratchet teeth of the overlapping branch bars are engaged with each other when any of the ratchet teeth do not engage with each other. Further, in relation with the situation that the position of engagement by the ratchet teeth is decided according to the pitch of the ratchet teeth, the diameter with which the stent made of polymer material is held takes discrete values, then the stent may not be perfectly adapted to the diameter of a blood vessel desired for treatment.

In order to prevent such a situation from occurring, it is advantageous that the pitch p of the ratchet teeth provided on the branch bar of one strut piece is different from the pitch p' of the ratchet teeth provided on the corresponding branch bar of the other strut piece that is to overlap on the former branch bar. FIG. 5 (a) shows a situation that the pitch p of the ratchet teeth provided on one branch bar is different from the pitch p' of the ratchet teeth provided on the other branch bar to overlap on the former branch bar (p'>p) in such a manner. FIG. 5 (b) shows a situation that the left end ratchet tooth (as shown) of the upper branch bar engages with the left end ratchet tooth of the lower branch bar and FIG. 5 (c) shows a situation that the ratchet tooth at the third position from the left end (shown by the dotted circle) from the left end of the upper branch bar engages with one at the third position of the lower branch bar. In such a manner, it is possible to secure engagement of either ratchet tooth of one branch bar with either ratchet tooth of the other mated branch bar and prevent a situation that the ratchet teeth do not engage with each other as a whole from occurring by making the pitches of a plurality of ratchet teeth on the branch bars overlapping each other different from each other. Further, the diameter of the expanded stent can be adjusted in finer manner that in the case decided by pitches of the ratchet teeth. Consequently, the stent can be applied to various patients or various affected parts.

While the struts 3 connected with links 2 as shown in FIG. 2 has been explained to have a substantially rhombic, closed shape, it is possible that the struts 3 have other shapes, such as hexagon, as explained later. Here, it is not necessarily required for the shape to be symmetric longitudinally or to be a closed shape. The requirement for a strut 3 is such that, in the constitution of a strut 3 connected to links 2 as shown in FIG. 3 (a), (b), the strut is deformed along with opening or closing of a pair of strut pieces 3a, 3a, branch bars 3b with ratchet teeth formed thereon are provided to protrude on the opposing sides of the pair of strut pieces respectively, and the mated branch bars 3b overlap each other with the ratchet teeth on the mated branch bars 3b coming to engage with each other. If this requirement is satisfied, function of a stent can be attained, even if the strut does not have a symmetric shape or a closed shape. Further, it is not required that all the struts have an identical shape.

The stent made of polymer material having a network constitution of strut-link as shown in FIG. 2 accomplish the function of a stent by mutual engagement of ratchet teeth formed on the sides of the branch bars provided on the two strut pieces that form a substantially Y shaped element with a link to protrude inwards so as to inhibit a movement such that the diameter of the stent is reduced. Meanwhile, it is also possible to allow an opened portion to be formed on the side of the stent and introduce another stent made of polymer material through the opened portion. This is adapted to indwelling two stents in the main vessel and branch vessel at a branched portion of a blood vessel.

This will be explained referring to FIG. 6. In the side face of a stent made of polymer material having strut-link constitution shown in FIG. 2, a balloon catheter BC, on which another stent made of polymer material with a reduced diameter is mounted, is inserted from inside to pass though between the left and right struts as shown. Then, the struts having a closed shape respectively are pushed aside in the left-right direction (axial direction of the stent) as shown in FIG. 6. Deformation of the struts at this time is made in a direction such that it is elongated in the circumferential direction of the stent, so that the ratchet teeth present a same movement and effect as in enlarging the diameter of the stent, enabling the struts to be deformed as well as the pushed aside state to be held. This provides an effect such that flow of blood into a branch vessel can be secured after indwelling of the stents. In such a manner, with stents made of polymer material having strut-link network constitution as shown in FIG. 2, two stents can be indwelled in a main vessel and a branch vessel at a branched portion of a blood vessel by inserting another stent through from inside of one stent.

Figure 7:
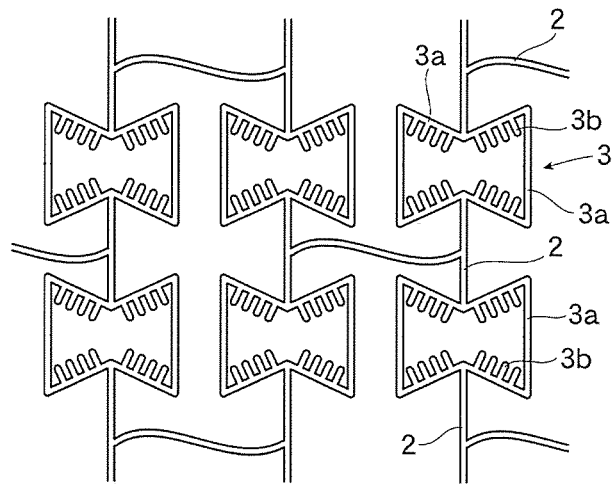
FIG. 7 (*a*) is a view showing a part of a stent made of polymer material having another strut configuration, FIG. 7 (*b*) is a view showing a part of the strut configuration in FIG. 7 (*a*), and FIG. 7 (*c*) is a view showing a state where the strut is elongated.
Figure 7:
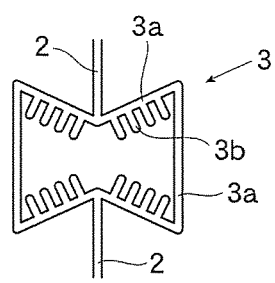
Figure 7:
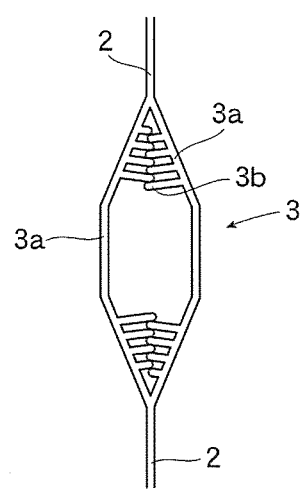

FIG. 7 (a) to (c) shows an example of a shape of a strut different from one shown in FIG. 2. In the case of the stent made of polymer material shown in FIG. 7 (a), a strut with a closed shape consists of six strut pieces 3a in a state where the stent is not expanded as shown in FIG. 7a, and each two strut pieces 3a and a link 2 in top side or bottom side of the strut forms an umbrella shape. A plurality of branch bars 3b are provided on the inner side (regarding the strut) of the two strut pieces 3a to protrude in a similar manner as in the case shown in FIG. 2, and ratchet teeth are formed on one side or both sides of respective branch bars 3b similarly.

When the diameter of a stent made of polymer material having a strut configuration shown in FIG. 7 (a) is enlarged, the struts shown in FIG. 7 (b) are pulled up in the longitudinal direction (as shown) via the links 2, 2 connected thereto at the upper and lower sites respectively, and the respective two strut pieces forming an umbrella shape on the upper and lower sides are reversed to have a Y shape respectively. As seen from the relation of ratchet teeth, the state shown in FIG. 7 (c) corresponds to one shown in FIG. 3 (a), from which the relation of the ratchet teeth advances further to one in which the left and right branch bars overlap each other so that ratchet teeth engage with each other as shown in FIG. 3 (b). With a stent made of polymer material having a strut-link configuration shown in FIG. 7 (a), the diameter of the stent is enlarged in transferring from the state in FIG. 7 (b) to one in Fig. (c), after which the ratchet teeth come to engage with each other. Consequently, expansion of the stent made of polymer material can be extended further by the amount corresponding to the former stage. While the two strut pieces 3a, 3a and a link 2 form an umbrella shape in an initial state in the case shown in FIG. 7 (a), the initial shape of the two strut pieces 3a, 3a and a link 2 may be a substantially T shape, with which amount of expansion becomes smaller than one with an umbrella shape.

Figure 8:
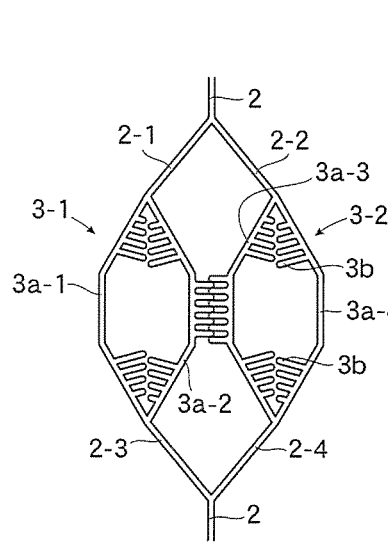
FIGS. 8 (*a*), (*b*) and (*c*) are views showing a strut-link arrangement of an element consisting of a set of two struts, each of which has a closed shape and has branch bars with ratchet teeth provided on its outside, where FIG. 8 (*a*) shows an initial state, FIG. 8 (*b*) shows a first elongated state and FIG. 8 (*c*) shows a second, further elongated state.
Figure 8:
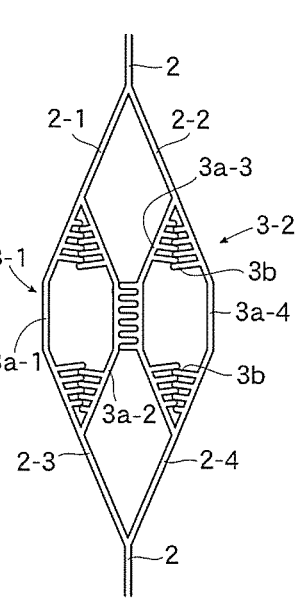
Figure 8:
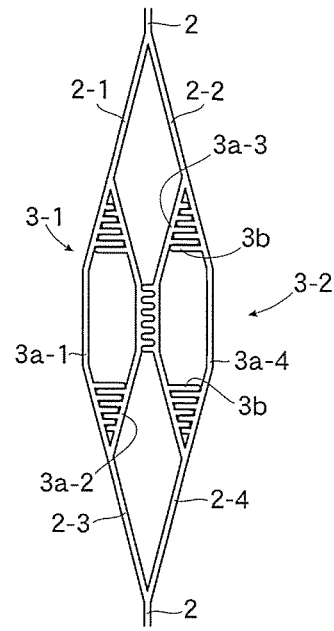

FIG. 8 (a) to (c) shows a varied arrangement for locking strut pieces by branch bars having ratchet teeth provided thereon. While two links 2, 2 are connected to a strut 3, one by one at each of top and bottom thereof, in the arrangement of strut-link shown in FIG. 2, the top sites of the two struts 3-1, 3-2 are connected, one by one, to each of links 2-1, 2-2 that are connected to and branched from an upper link 2 and the bottom sites of the two struts 3-1, 3-2 are connected, one by one, to each of links 2-3, 2-4 that are connected to and branched from a lower link 2 in the arrangement of strut-link shown in FIG. 8 (a).

The struts 3-1, 3-2 have a closed hexagonal shape and the struts are similar as the case of a strut shown in FIG. 2 in that branch bars with ratchet teeth formed thereon are provided to protrude on the inner sides of the upper two opposing strut pieces (upper portions of the strut pieces 3a-1, 3a-2; and 3a-3, 3a-4 respectively) and the lower two opposing strut pieces (lower portions of the strut pieces 3a-1, 3a-2; and 3a-3, 3a-4 respectively) and engagement with each other of the ratchet teeth formed on the branch bars 3b inhibits movement of the strut pieces in the direction of causing the strut pieces to open. Branch bars with ratchet teeth formed thereon are provided to protrude also on the outer side of each of the opposing strut pieces 3a-2, 3a-3 (middle portions of the strut pieces) of the neighboring struts 3-1, 3-2 respectively, and the ratchet teeth on the branch bars come to engage with each other when the struts 3-1, 3-2 are deformed so that the strut pieces 3a-2, 3a-3 (middle portions of the strut pieces) come close together.

The connecting portions of links are designed such that the portions where the upper link 2 branches into links 2-1, 2-2 and the lower link 2 branches into links 2-3, 2-4 have a configuration to be more deformable, that is, more flexible to deformation respectively compared with the portions where the links 2-1, 2-2 and links 2-3, 2-4 are connected to the strut pieces 3a-1, 3a-2 and links 3a-3, 3a-4 respectively.

With a stent made of polymer material having a strut-link network constitution shown in FIG. 8 (*a*), when the stent is deformed to enlarge its diameter, that is, deformed to elongate the upper and lower links 2, 2 (as shown) upwards and downwards respectively, struts 3-1 and 3-2 are caused to come near to each other before deformation of themselves and then move further so that the branch bars provided on the outer sides of the strut pieces 3a-2, 3a-3 (middle portions of the strut pieces) respectively overlap each other with the ratchet teeth formed thereon engaging with each other in the first step, because the portions where the upper link 2 branches into links 2-1, 2-2 and the lower link 2 branches into links 2-3, 2-4 are more deformable.

When the stent is deformed further to enlarge its diameter, the portions where the links 2-1, 2-2 and links 2-3, 2-4 are connected to the strut pieces 3a-1, 3a-2 and strut pieces 3a-3, 3a-4 respectively are deformed in the next step, so that the struts 3-1 and 3-2 are deformed to be elongated upwards and downwards and to close the upper portions of the two strut pieces and the lower portions of the two strut pieces respectively as shown in FIG. 8 (*c*). Due to this, the branch bars provided on the inner sides of these strut pieces respectively move to overlap each other with the ratchet teeth formed thereon engaging with each other.

With the stent made of polymer material having a strut-link network constitution shown in FIG. 8 (*a*), two steps of action of ratchet teeth engaging with each other are performed in enlarging the diameter of the stent, so that the extent of action the stent presents can be widened and the range of diameter of the stent to be fixed can be enlarged.

Figure 9:
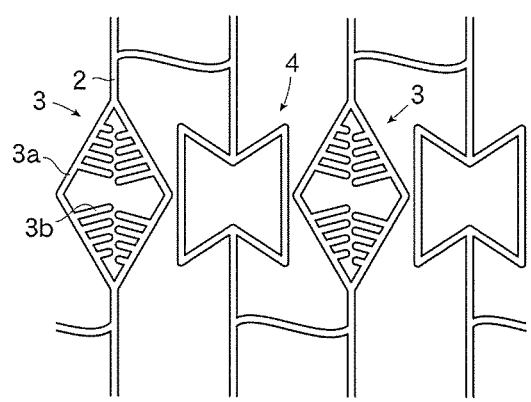
FIGS. 9 (*a*) and (*b*) are views showing a strut-link arrangement, in which a complementary strut is disposed between two struts, where FIG. 9 (*a*) shows an initial state and FIG. 9(*b*) shows an elongated state.
Figure 9:
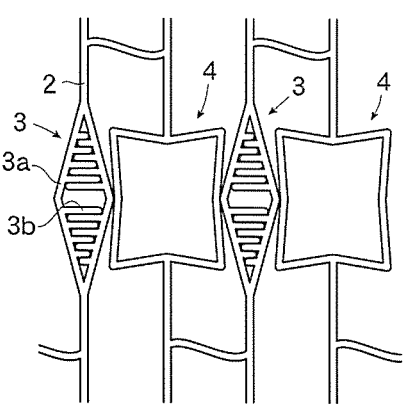

FIG. 9 (*a*), (*b*) shows an example of strut-link arrangement composed to include struts serving for a complementary action along with those presenting locking action by engagement of ratchet teeth with each other. In FIG. 9 (*a*), reference number 3 denotes struts in which branch bars 3b with ratchet teeth formed thereon are provided to protrude on the inner sides of the strut pieces 3a similarly as the one shown in FIG. 2. Here, a complementary strut 4 is disposed between two left and right struts 3, 3 as shown to form an element of the stent and then a plurality of such elements are connected by links 2 to constitute a stent having a strut-link network constitution as a whole. The complementary strut 4 is different from the strut 3 in that branch bars are not provided on the inner side of the strut pieces and the connecting portion of the strut pieces with a link does not form a Y shape but form an umbrella shape. The portions approximating each other in left-right direction may be integrated with a connection.

When the stent made of polymer material having a constitution shown in FIG. 9 (*a*) is deformed to enlarge the diameter of the stent, the strut 3 is deformed so that it is being pulled up by the upper and lower links 2, 2, and elongated upwards and downwards and, along with this, is narrowed in the left-right direction as shown in FIG. 9 (*b*). Meanwhile, in the complementary strut 4, the upper and lower two strut pieces forming an umbrella shape respectively, being pulled up by the upper and lower links 2, 2, are flattened. Due to this, the width of the strut 4 in the left-right direction is enlarged, so that the strut pieces on both of the left and right sides of the strut 4 act so as to press the strut 3 from both sides. With such pressing action on the strut 3 from left-right sides, the effect to narrow the width of the two strut pieces towards the sides of their connection with the respective links is strengthened, so that the effect of locking by overlapping of the branch bars on the inner sides of the strut pieces with the ratchet teeth engaging with each other is strengthened and secured. In such a manner, the constitution having complementary struts allows the ratchet teeth formed on the branch bars provided on the inner sides of the struts pieces to engage with each other more securely.

The stent made of polymer material having a strut-link network constitution as explained above is so arranged that, in deformation of the stent to enlarge its diameter, the paired strut pieces pulled up by the links in the circumferential direction is caused to narrow the width of the strut in the axial direction, thus causing the branch bars provided on the inner sides of the paired strut pieces to overlap each other with the ratchet teeth formed on the branch bars engaged with each other. As for such a constitution of struts, the branch bars provided on the mated strut pieces are basically so arranged to move in the axial direction of the stent made of polymer material in enlarging the diameter of the stent.

Figure 10:
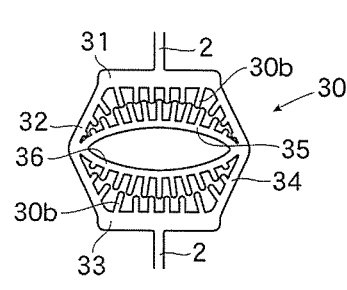
FIG. 10 (*a*) is a view showing another configuration of a strut in which branch bars move in a different manner for ratchet teeth to engage with each other, and FIG. 10 (*b*) is a view showing a state where the strut is deformed so that branch bars overlap each other.
Figure 10:
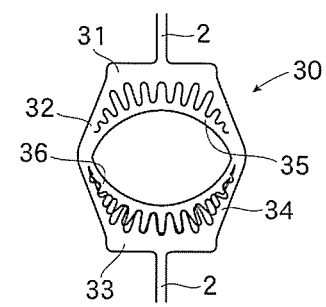

In contrast to this, another arrangement of a strut-link constitution can be also considered such that, in enlarging the diameter of the stent made of polymer material, the branch bars provided on the mated strut pieces basically move in the circumferential direction of the stent and overlap each other with the ratchet teeth formed thereon engaging with each other. FIG. 10 (*a*), (*b*) shows such an arrangement of a strut 30 connected by links 2, 2. This strut 30 is constituted such that two strut pieces 31 and 33 connected to an upper or lower link 2, 2 respectively, two strut pieces 32 and 34 disposed between the formers and having a "〈" or reversed "〈" shape respectively are connected among them to form a closed hexagonal shape as shown and further a strut piece 35 protruding convex upwards and a strut piece 36 protruding convex downwards are connected in a manner bridging between the bending points of the strut pieces 32 and 34 respectively.

While the strut pieces 31 and 33 connected to the upper or lower link 2 respectively are formed to be thicker and less easily deflected to be bent, the strut pieces 32, 34, 35 and 36 are formed to be thinner and more easily deflected to be bent. In the upper part of the strut 30, a plurality of branch bars 30b protruding towards the strut piece 35 are provided on the sides of the upper strut piece 31 and the upper portions of the strut pieces 32 and 34 connected to the strut piece 31 respectively, and a plurality of branch bars 30b protruding towards the upper strut piece 31 and the upper portions of the strut pieces 32 and 34 connected to the strut piece 31 respectively are provided on the side of the strut piece 35. A plurality of ratchet teeth is formed on one side or both sides of each of these branch bars and the ratchet teeth come to engage with each other when the paired branch bars overlap each other.

In the lower part of the strut 30, the strut pieces are constituted in a similar manner. While the strut pieces 33 connected to the lower link 2 is formed to be thicker and less easily deflected to be bent, the lower portions of the strut pieces 32 and 34 connected to the strut piece 33 and strut piece 36 bridging between the bending points of the strut pieces 32 and 34 are formed to be thinner and more easily deflected to be bent. A plurality of branch bars 30b protruding towards the strut piece 36 are provided on the sides of the lower strut piece 33 and the lower portions of the strut pieces 32 and 34 connected to the strut piece 33 respectively, and a plurality of branch bars 30b protruding towards the lower strut piece 33 and the lower portions of the strut pieces 32 and 34 connected to the strut piece 31 respectively are provided on the side of the strut piece 36. A plurality of ratchet teeth is formed on one side or both sides of each of these branch bars and the ratchet teeth come to engage with each other when paired branch bars overlap each other.

When a stent made of polymer material having an arrangement shown in FIG. 10 (a), in which a plurality of struts 30 are connected by links 2, is caused to enlarge its diameter, the links 2 pull up the struts 30 in the circumferential direction of the stent. With this, while the strut pieces 31 and 33 that are thicker and less easily deformed remain as they are, the strut pieces 32 and 34 that are thinner and easily deformed are elongated to have a flatter shape so that the strut pieces 35 and 36 bridging between the bending points are compressed to increase upward and downward curvatures respectively, thus resulting in a state shown in FIG. 10 (b). At this time, the strut piece 35 is deformed to come near to the strut piece 31 and the upper portions of the strut pieces 32 and 34 connected to the strut piece 31 respectively, coming to a state that the branch bars 30b overlap each other with the ratchet teeth formed thereon engaging with each other.

The strut pieces in the lower part of the strut 30 as shown are deformed in a similar manner. When the stent made of polymer material is caused to enlarge its diameter, the strut piece 36 is deformed to come near to the strut piece 33 and the lower portions of the strut pieces 32 and 34 connected to the strut piece 33 respectively, coming to a state that the branch bars 30b overlap each other with the ratchet teeth formed thereon engaging with each other. In such a manner, in a stent made of polymer material having a strut-link constitution as shown in FIG. 10 (a), the branch bars provided on the mated strut pieces are basically so arranged to move in the circumferential direction of the stent made of polymer material in enlarging the diameter of the stent, coming to a state that the branch bars overlap each other with the ratchet teeth formed thereon engaging with each other.

Figure 11:
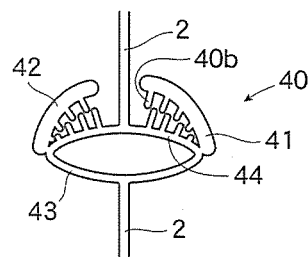
FIG. 11 (*a*) is a view showing a still another configuration of a strut in which branch bars moves in a different manner for ratchet teeth to engage with each other, and FIG. 11 (*b*) is a view showing a state where the strut is deformed so that branch bars overlap each other.
Figure 11:
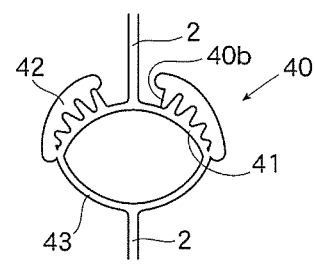
Figure 12:
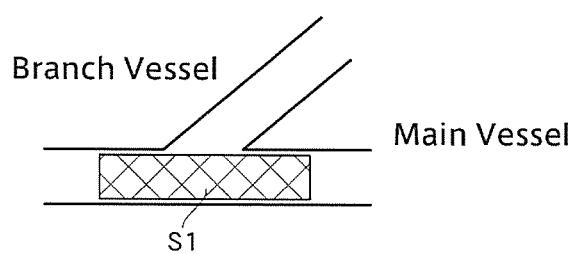
FIGS. 12 (*a*), (*b*) and (*c*) are views explaining a manner that stents are indwelled in a site of a blood vessel having a branched portion, where FIG. 12 (*a*) shows a state where a stent is indwelled at a branched portion in a main vessel so as to extend covering the branched portion, FIG. 12 (*b*) shows a state where another stent is introduced through the side of the indwelled stent to the branch vessel, and FIG. 12 (*c*) shows a state where stents are indwelled in the main vessel and the branch vessel respectively.
Figure 12:
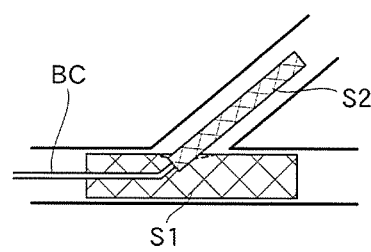
Figure 12:
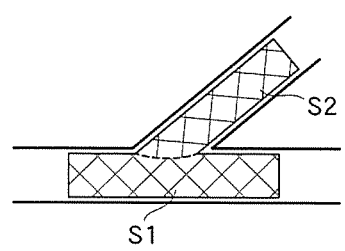

FIG. 11 (a), (b) shows still another arrangement of a strut. FIG. 11 (a) shows a strut 40 connected to links 2 in a stent made of polymer material, in which a strut piece 43 bent in a downwards convex manner and a strut piece 44 bent in an upwards convex manner are connected at both ends thereof and one end of each of two strut pieces 41 and 42 bent in an upwards convex manner is connected, in a cantilever manner, to one or the other of the connecting points of the strut pieces 43 and 44. Here, the other ends of the strut pieces 41 and 42 are directed to come close together and each of the strut pieces 41 and 42 is connected to have some angle to the strut piece 44. While the strut pieces 41 and 42 connected in a cantilever manner are formed to be thicker and less easily deformed to be bent, strut pieces 43 and 44 are formed to be thinner and more easily deformed to be bent.

The strut piece 44 is connected to the upper link 2 at its center position and the strut piece 43 is connected to the lower link 2 at its center position. A plurality of branch bars 40b are provided on the upper side of the strut piece 44 to protrude towards either of the strut pieces 41 and 42 and a plurality of branch bars 40b are provided on the lower sides of the strut pieces 41 and 42 to protrude towards the strut piece 44 respectively. A plurality of ratchet teeth is formed on one side or both side of each of these branch bars 40b so that the ratchet teeth come to engage with each other when the mated branch bars overlap each other.

When the stent made of polymer material having a constitution, in which a plurality of struts with a configuration shown in FIG. 11 (a) are connected by links to have a network constitution, is deformed to enlarge its diameter, the upper and lower links 2, 2 pull up the strut 40 in the circumferential direction of the stent. Due to this, the strut pieces 43 and 44 that are more easily deflected to be bent are deflected so as to increase the extent of downward convexity or upward convexity respectively as shown in FIG. 11(b). Along with this, both end portions of the strut piece 44 come near to either of the strut pieces 41 and 42 decreasing the angle between them. For this sake, the branch bars provided to protrude on the side of the strut piece 44 and on the sides of the strut pieces 41 and 42 respectively come to overlap each other with the ratchet teeth formed on the branch bars engaging with each other.

The stent made of polymer material as explained above is constituted to have a network constitution in which a plurality of struts is connected by links. In order to manufacture such a stent made of polymer material, it is necessary to perform working on a tube shaped material for a stent so as to cause the portions of the struts and links constituting the stent to remain while removing the other part. While methods of photolithography employed for working on plane materials is not so adapted for using to perform fine working to form such a configuration of struts with ratchet teeth on branch bars and links, such a configuration can be formed through laser beam machining as another method employed in manufacturing a stent made of metal material. Further, finer working can be made by using a cylindrical reactive ion etching technology as a method developed by the inventor et al. (Journal of Micromechanics and Microengineering, 24 (2014) 055022, pp. 1-8, doi:10.1088/0960-1317/24/5/055022).

What is claimed is:

1. A stent made of a first polymer material having a ratchet and formed to have a cylindrical shape as a whole in which a plurality of struts are connected by links to each other to form a network constitution, and each of the struts comprises a plurality of strut pieces connected to each other; wherein
    the plurality of strut pieces in each of the struts include at least one pair of strut pieces_connected by one of the links extending in a circumferential direction of the stent to form a Y shape,
    a plurality of branch bars is provided successively side by side on both of opposing sides of each pair of strut pieces so as to protrude from one of the strut pieces towards the other of the strut pieces in each pair of strut pieces,
    a plurality of ratchet teeth is formed on one side or both sides of each of the plurality of branch bars, movement towards opening of each pair of strut pieces is inhibited so that deformation of the stent to reduce a diameter of the cylindrical shape of the stent is also inhibited by engagement of the ratchet teeth formed on the branch bars on one of the strut pieces of each pair of strut pieces and the ratchet teeth fon ied on the branch bars on the other one of the strut pieces of each pair of strut pieces with each other, movement towards closing of each pair of strut pieces is allowed so that deformation of the stent to enlarge the diameter of the cylindrical shape of the stent is also allowed, and the network constitution in which the plurality of struts are connected by the links is configured such that:

the stent made of the first polymer material has a maximum expanded diameter such that the stent is configured to be placed in a site having an inner diameter smaller than the maximum expanded diameter, and when a catheter is introduced between two struts disposed in a neighboring relation in an axial direction of the stent, the two struts disposed in the neighboring relation are deformed to be elongated in a circumferential direction of the stent as well as deformed to enlarge a distance between the two struts in the axial direction of the stent so that a configuration of the struts and the links is maintained to allow the catheter and another stent made of a second polymer material to be indwelled thereafter between the two struts, and two adjacent ratchet teeth are separated by a groove.

2. The stent made of the first polymer material having the ratchet according to claim 1, wherein at least one pair of the pair of strut pieces are arranged such that one strut piece is more easily deflected to be bent and one strut piece less easily deflected to be bent are spaced apart in the circumferential direction of the stent and connected to each other at end sides, in deformation to enlarge the diameter of the cylindrical shape of the stent made of polymer material, the more easily deflected strut piece of each pair of strut pieces is deflected by being pulled up in the circumferential direction of the stent via the connected link so as to come close to the less easily deflected strut piece, thus bringing a state where the branch bars protruding from one side of the more easily deflected strut piece and protruding from the other side of the less easily deflected strut piece are brought into contact with each other, wherein the ratchet teeth formed on the sides of the branch bars are engaged with each other.

3. The stent made of the first polymer material having the ratchet according to claim 1, wherein the plurality of ratchet teeth formed on the one side or on both of the sides of the branch bars provided to protrude on the opposing sides of each pair of strut pieces are configured such that a pitch of the ratchet teeth fonned on one of the branch bars is different from a pitch of the ratchet teeth formed on the other of the branch bars that is engaged with the one branch bar.

4. The stent made of the first polymer material having the ratchet according to claim 1, wherein connecting portions of each pair of strut pieces with the links or bending portions between each pair of strut pieces involved in deformation of the struts to enlarge or reduce the diameter of the stent made of the first polymer material are formed to have partly a curved shape.

* * * * *